United States Patent [19]

Redmore et al.

[11] 4,104,293

[45] Aug. 1, 1978

[54] OIL-SOLUBLE CHROMIUM COMPOSITIONS

[75] Inventors: Derek Redmore, Ballwin; Frederick T. Welge, Webster Groves, both of Mo.

[73] Assignee: Petrolite Corporation, St. Louis, Mo.

[21] Appl. No.: 683,407

[22] Filed: May 5, 1976

[51] Int. Cl.² ............................................. C07F 11/00
[52] U.S. Cl. ................................. 260/438.5 R; 252/1; 252/33; 252/33.2; 252/354; 252/389 R; 260/414
[58] Field of Search ................ 260/438.5 R, 414, 252; 252/354, 33, 1, 389, 33.2

[56] References Cited

U.S. PATENT DOCUMENTS

| | | | |
|---|---|---|---|
| 1,438,101 | 12/1922 | Divine | 260/438.5 R X |
| 1,986,044 | 1/1935 | Casaburi | 260/438.5 R X |
| 2,121,485 | 6/1938 | Mc Allister et al. | 260/438.5 R X |
| 2,367,470 | 1/1945 | Neely et al. | 252/33 |
| 2,428,356 | 10/1947 | Chester et al. | 260/438.5 R |
| 2,507,030 | 5/1950 | Lynch | 260/438.5 R X |
| 2,760,970 | 8/1956 | Le Suer | 260/438.5 R X |
| 2,794,829 | 6/1957 | van der Waarden et al. | 260/438.5 X |
| 3,415,870 | 12/1968 | Kangas et al. | 260/438.5 R X |
| 3,649,659 | 3/1972 | Otto et al. | 260/438.5 R X |
| 3,932,285 | 1/1976 | Ceprini et al. | 252/431 C |

OTHER PUBLICATIONS

Chemical Abstracts, 47, 10818c(1953).
Chemical Abstracts, 74, 129802v(1971).

*Primary Examiner*—Helen M. S. Sneed
*Attorney, Agent, or Firm*—Sidney B. Ring; Hyman F. Glass

[57] ABSTRACT

This invention relates to the preparation of oil-soluble chromium compositions of high chromium content, such as from about 15 to 30% chromium; to the resulting products; and to the use of such products, for example, as fuel additives, such as additives employed in turbine fuel as corrosion inhibitors, and other uses.

15 Claims, No Drawings

OIL-SOLUBLE CHROMIUM COMPOSITIONS

Oil-soluble chromium compositions have been prepared by a wide variety of methods. One composition is described in U.S. Pat. No. 3,932,285 as follows:

"Stable solutions that contain at least 7.5% by weight of dissolved chromium comprise an organic solvent and a mixture of chromium salts that contains at least one chromium salt of a straight-chain aliphatic monocarboxylic acid having 5 to 10 carbon atoms and at least one chromium salt of a branched-chain aliphatic monocarboxylic acid having 5 to 10 carbon atoms."

We have now discovered a method for the preparation of oil-soluble chromium compositions containing high chromium concentrations such as for example from about 15 to 30% chromium. Our process comprises reacting chromium oxide with a solution of a sulfonic acid or with a sulfonic acid in conjunction with a carboxylic acid. Carboxylic acids alone are not suitable. Although not essential, it is advantageous to have water present since it facilitates more efficient dispersion. In practice water is employed, based on chromium oxide, in weight ratios of at least about 15%, such as about 15 to 45%, for example from about 18 to 40%, but preferably from about 20 to 35%. In practice, the reaction mixture is heated and the solvent and water present are removed by distillation.

A wide variety of sulfonic acids can be employed for example sulfonic acids of the idealized formula $R\,SO_3H$ where R is preferably a hydrocarbon moiety, having for example about 10 to 60 carbons, such as from about 12 to 50, for example from about 12 to 40, but preferably only 14 to 30 carbons.

Examples of hydrocarbon moieties of the sulfonic acids include alkyl, aryl, alkaryl, aralkyl, cycloalkyl, etc. groups, as illustrated by the following specific examples:

octyl
decyl
dodecyl
tetradecyl
hexadecyl
octadecyl
octyl phenyl
nonylphenyl
decylphenyl
dodecylphenyl
tetradecylphenyl
dipropylnaphthyl
dibutylnaphthyl
dioctylnaphthyl, etc.

Although we prefer a hydrocarbon moiety which has a molecular weight of less than about 300, the higher sulfonic acid may be employed.

The sulfonic acid may also have more than 1 $SO_3H$ groups, for example $R(SO_3H)_n$.

Although not required, carboxylic acids may be employed in conjunction with sulfonic acids. Suitable carboxylic acids which can be used in preparing the chromium oxide dispersions include naphthenic acids, such as the substituted cyclopentane monocarboxylic acids, the substituted cyclohexane monocarboxylic acids and the substituted aliphatic polycyclic monocarboxylic acids containing at least 15 carbon atoms. Specific examples include cetyl cyclohexane carboxylic acids, dioctyl cyclopentane carboxylic acids, dilauryl decahydronaphthalene and stearyl-octahydroindene carboxylic acids and the like and oil-soluble salts thereof. Suitable oil-soluble fatty acids are those containing at least about 8 carbon atoms. Specific examples include 2-ethyl hexanoic acid, pelargonic acid, oleic acid, stearic acid, palmitoleic acid, linoleic acid and ricinoleic acid. Naturally occurring mixtures of predominantly unsaturated fatty acids, such as tall oil fatty acids, are particularly suitable. Examples of commercially available tall oil fatty acids include the "Crofatols," available from Crosby Chemical Company and the "Acintols," available from Arizona Chemical Company.

The molar ratio of sulfonic acids to carboxylic acids can vary widely, such as from about 10:1 to 1:10, for example from about 5:1 to 1:5, but preferably from about 4:1 to 1:4.

Volatile solvents employed herein are hydocarbon solvents having a boiling point at normal atmospheric pressure of less than about 400° F. Some specific examples of such solvents are: petroleum naptha, hexane, heptane, octane, benzene, toluene, glycol ethers, monohydric alcohols containing from about 1 to about 6 carbon atoms and the like. Very desirable solvents are hexane, heptane, benzene, toluene, xylene, butanol and the monomethyl ether of ethylene glycol.

Suitable chromium oxides useful in this invention can be characterized by x-ray diffraction patterns. Using $CuK_{1,2}$ source 1.5405 and nickel filter the following spacings were obtained for a hydrated chromium oxide.

3.25 – 3.35
2.30 – 2.45
1.94 – 1.96
1.48 – 1.50

A suitable hydrated chromium oxide such as Hercules X-1010 gave following analysis: $Cr_2O_3$ 79%, water of hydration 14%, moisture 3%, $B_2O_3$ 3.5%, Na 0.5%.

Chromium oxides useful in this process are prepared by reduction of dichromates for example with boric acid or reducing agents such as sulfur or carbon. It appears that roasting as is commonly employed in preparing chromium oxide pigments is undesirable.

The following examples are presented for purposes of illustration and not of limitation.

EXAMPLE 1

To a solution of stearic acid (3.3g) and dodecylbenzene sulfonic acid (14.7g) in xylene (150 ml) was added hydrated chromium oxide (K&K Laboratories) (54g) with stirring over a period of 20 minutes. After continuing to stir at room temperature for 1½ hrs. the mixture was heated to reflux. Water and xylene (60 ml) were removed and the product centrifuged at 2200 rpm to remove 2.2g of insolubles. The solution was concentrated further and acetic acid (3 ml) added to reduce viscosity yielding a clear free flowing liquid 144.5g. The chromium content was 16.9%.

EXAMPLE 2

To a solution of stearic acid (6.6g) and dodecyl benzenesulfonic acid (29.4g) in xylene (200 ml) was added hydrated chromium oxide (Pfizer GH-9869) (54g) in 15 mins. After stirring 1 hour at room temperature the dispersion was heated to reflux and water and xylene removed. Centrifugation removed 2g of insolubles. After addition of acetic acid (3.5 ml) there was obtained a free-flowing liquid (146.6g) with chromium content of 19.8%.

EXAMPLE 3

To a solution of dodecylbenzenesulfonic acid (14.7g) and stearic acid (3.3g) in xylene (140 ml) was added hydrated chromium oxide (Hercules X-1010) (54g) in 15 minutes with efficient stirring. The mixture was heated to reflux after stirring at room temperature for 1½ hrs. Removal of water and xylene followed by centrifugation gave 6g of insoluble and 126g of clear free flowing liquid with chromium content of 19.9%.

EXAMPLE 4

Effect of Water

This example was identical to Example 3 except that water (4g) was added to the solution of acids prior to the addition of the chromium oxide. By the work-up procedure of Example 3 there was obtained 110g of liquid product with chromium content 24.5% and an insoluble residue of 4g.

The addition of water gives a product with higher chromium content and less insoluble residue.

EXAMPLE 5

To a solution of dodecylbenzenesulfonic acid (18.4g) in water (4g) and xylene (140 ml) was added hydrated chromium oxide (Hercules X-1010) (54g) during 10 minutes. The mixture was heated to reflux and water and xylene removed by distillation. Centrifugation removed 4g of insoluble and 106g of liquid product to which was added acetic acid (2 ml) to lower the viscosity. The product contained 25% chromium.

EXAMPLE 6

Effect of Solvent

This preparation was identical to that of Example 5 except that hexane was substituted for xylene. There was obtained 118g of liquid product with chromium content 23.1% and 3g of solid residue.

EXAMPLE 7

Effect of Solvent

This preparation was identical to that of Example 5 except that kerosene was substituted for xylene. There was obtained 116g of liquid product with chromium content 24.7% and 2g of insoluble sediment.

EXAMPLE 8

To a solution of pentadecylbenzenesulfonic acid (21.0g) in xylene (140 ml) and water (4g) was added hydrated chromium oxide (Hercules X-1010) (54g) in 20 minutes. After stirring 1 hour at room temperature the mixture was heated to reflux and xylene and water removed. Centrifugation removed 6g of insolubles. Addition of acetic acid (2 ml) gave a clear free flowing liquid (110g) with chromium content 24.4%.

EXAMPLE 9

Use of a petroleum sulfonic acid

By the procedure of Example 5 in which Morco H-50 (58.3g) (Marathon Morco Co.) was substituted for dodecylbenzenesulfonic acid a clear product was obtained (107.5g) with chromium content 24.1%. Residue from centrifugation was 6g.

It can be seen from the above examples that although combinations of carboxylic acid and sulfonic acid as dispersants give useful products, the use of sulfonic acid alone is as good or better. The addition of water during dispersion although not essential allows the incorporation of higher levels of chromium into the final products.

Chromium dispersions produced by the process of the present invention are useful as fuel oil additives, jet fuel additives, motor fuel additives, lubricant additives and the like. The dispersions of the present invention are particularly useful since such dispersions contain substantial amounts of chromium in a clear bright dispersion suitable for use in high quality motor oils and the like.

The compositions of this invention are particularly effective in the inhibition of vanadium corrosion in gas turbines.

Although the chromium-containing compositions of this invention are strictly speaking dispersions, their behaviour resembles that of solutions. Thus, the compositions are clear to the naked eye and can be diluted with oils such as hydrocarbon solvents to give clean solutions on dilution and are thus oil-soluble compositions.

We claim:

1. A process of preparing oil-soluble chromium compositions having from about 15% to about 30% chromium which comprises reacting hydrated chromium oxide obtained by the reduction of dichromates with an oil-soluble sulfonic acid having about 10 to 60 carbon atoms in a volatile solvent by stirring for a period of about 1 to about 1.5 hours at room temperature and then heating to reflux, removing water and solvent and finally centrifuging to remove insolubles.

2. The process of claim 1 where the chromium oxide reacted is prepared by the reduction of dichromates with borates or sulfur or carbon reducing agents.

3. The process of claim 1 where water is employed in the reaction in a weight ratio of about 15% to about 45% based on the chromium oxide.

4. The process of claim 2 where substantially no water is employed in the reaction.

5. The process of claim 1 where a carboxylic acid is also employed in the reaction in a molar ratio of sulfonic acid to carboxylic acid of about 10:1 to 1:10.

6. The process of claim 5 where the carboxylic acid is stearic acid.

7. The process of claim 1 where the sulfonic acid is dodecylbenzenesulfonic acid.

8. The process of claim 1 where the sulfonic acid is pentadecylbenzenesulfonic acid.

9. The reaction product of claim 1.

10. The reaction product of claim 5.

11. The reaction product of claim 6.

12. The reaction product of claim 7.

13. The reaction product of claim 8.

14. The process of claim 3 where the weight ratio of the water is about 20% to 35% based on the weight of the chromium oxide.

15. The process of claim 5 where the molar ratio of sulfonic acid to carboxylic acid is about 4:1 to about 1:4.

* * * * *